(12) United States Patent
Goldschmidt

(10) Patent No.: US 9,713,503 B2
(45) Date of Patent: Jul. 25, 2017

(54) SURGICAL UTILITY CONNECTOR

(71) Applicant: Novartis AG, Basel (CH)

(72) Inventor: Alan B. Goldschmidt, Mission Viejo, CA (US)

(73) Assignee: Novartis AG, Basel (CH)

(*) Notice: Subject to any disclaimer, the term of this patent is extended or adjusted under 35 U.S.C. 154(b) by 742 days.

(21) Appl. No.: 14/096,347

(22) Filed: Dec. 4, 2013

(65) Prior Publication Data
US 2015/0150546 A1   Jun. 4, 2015

(51) Int. Cl.
| | | |
|---|---|---|
| *A61M 25/16* | (2006.01) | |
| *A61M 25/18* | (2006.01) | |
| *A61M 39/00* | (2006.01) | |
| *A61M 39/10* | (2006.01) | |
| *A61B 19/00* | (2006.01) | |
| *A61B 90/90* | (2016.01) | |
| *A61B 90/98* | (2016.01) | |
| *A61B 17/00* | (2006.01) | |

(52) U.S. Cl.
CPC ............. *A61B 19/44* (2013.01); *A61B 90/90* (2016.02); *A61B 90/98* (2016.02); *A61B 2017/00225* (2013.01); *A61B 2017/00482* (2013.01); *A61B 2017/00876* (2013.01)

(58) Field of Classification Search
CPC .......... A61B 2017/00876; A61B 17/00; A61B 2017/00199; A61B 2017/00225; A61B 2017/00411; A61B 2017/00477; A61B 2017/00482
See application file for complete search history.

(56) References Cited

U.S. PATENT DOCUMENTS

| | | | |
|---|---|---|---|
| 7,443,296 B2 | 10/2008 | Mezhinsky et al. | |
| 7,504,918 B2 | 3/2009 | Prendergast et al. | |
| 7,625,014 B2 | 12/2009 | Turner | |
| 8,561,280 B2 | 10/2013 | Diao et al. | |
| 8,585,681 B2 * | 11/2013 | Boenig | A61M 1/285 604/533 |
| 8,715,305 B2 * | 5/2014 | Pate | A61B 17/0057 600/16 |
| 8,777,931 B2 | 7/2014 | Davis et al. | |

(Continued)

FOREIGN PATENT DOCUMENTS

| | | |
|---|---|---|
| DE | 10 2013004591 | 9/2014 |
| EP | 1389173 | 2/2004 |

(Continued)

*Primary Examiner* — Rebecca E Eisenberg

(57) ABSTRACT

A surgical utility connector is detectable by a surgical utility supplying device to indicate connection with the surgical utility supplying device. The surgical utility connector includes a first connecting region, a second connecting region, and a detection region between the first connecting region and the second connecting region. A utility channel may pass a utility from the surgical utility supplying device. The utility channel may extend through the first connecting region, the detection region, and the second connecting region. The surgical utility connector also may include a magnetic element disposed in the detection region and surrounding the utility channel. The magnetic element may have a field detectable by the surgical utility supplying device when the surgical utility connector is connected to the surgical utility supplying device.

12 Claims, 7 Drawing Sheets

(56) References Cited

U.S. PATENT DOCUMENTS

| | | |
|---|---|---|
| 2002/0170731 A1 | 11/2002 | Garber et al. |
| 2007/0179473 A1* | 8/2007 | Masters ............ A61M 25/0097 604/533 |
| 2011/0018254 A1 | 1/2011 | Kuck et al. |
| 2011/0196291 A1 | 8/2011 | Vischer et al. |
| 2013/0092247 A1 | 4/2013 | Lee et al. |
| 2015/0105798 A1* | 4/2015 | Lohmeier .......... A61B 19/2203 606/130 |
| 2015/0250933 A1* | 9/2015 | Kerkhoffs .............. A61N 1/372 604/500 |
| 2016/0045365 A1 | 2/2016 | Foster et al. |

FOREIGN PATENT DOCUMENTS

| | | |
|---|---|---|
| EP | 2046226 | 4/2009 |
| EP | 2255120 | 12/2010 |
| EP | 1762541 B1 | 1/2011 |
| EP | 1996851 B1 | 11/2011 |
| EP | 1799610 B1 | 11/2012 |
| EP | 2533823 | 12/2012 |
| EP | 2581061 | 4/2013 |
| EP | 2751371 | 7/2014 |
| WO | WO 2007/002508 | 1/2007 |
| WO | WO 2007/003770 | 1/2007 |
| WO | WO 2008/016803 | 2/2008 |
| WO | WO 2013/033196 | 3/2013 |

\* cited by examiner

SURGICAL UTILITY CONNECTOR

BACKGROUND

The devices, systems, and methods disclosed herein relate generally to surgical utility connectors, and more particularly, to surgical utility connectors configured to connect a surgical utility supplying device to a surgical implement.

Surgical implements, such as surgical imaging probes, surgical drills, surgical vitrectomy probes, and the like, are connected to a surgical utility supplying device to receive utility, such as laser imaging light, compressed air, or the like. The surgical implements are connected to the surgical utility supplying device via surgical utility connectors.

To prevent the mis-supply of utility, the surgical utility supplying device may determine whether a surgical implement is properly connected to the surgical utility supplying device before supplying the utility to the surgical implement. The surgical utility supplying device may detect the presence of a portion of the surgical utility connector to determine whether the surgical implement is properly connected. According to a first technique, some conventional systems use an internal optical sensor to detect the presence of the surgical utility connector. For example, when a portion of the surgical utility connector is inserted into the surgical utility supplying device, the portion of the surgical utility connector may block a light beam of the internal optical sensor to indicate that the surgical utility connector is connected. Nevertheless, some surgical utility connectors, such as pneumatic surgical implements, do not have portions that are inserted into the surgical utility supplying device. Thus, optical sensing of the connectors may not work for this type of surgical utility connectors.

According to a second technique, some conventional systems detect the surgical utility connector using Radio Frequency Identification (RFID) tags. An RFID scanner/detector may be installed in the surgical utility supplying device to detect an RFID tag embedded in the surgical utility connector. Nevertheless, in the RFID detection technique, the RFID scanner/detector may be required to continuously poll the RFID tag embedded in the surgical utility connector to monitor continuous connection. Further, if the surgical utility connector is disconnected from the surgical utility supplying device, the RFID scanner/detector may not detect the disconnection until the next polling cycle, which can delay the shut off of the utility to prevent hazard.

The present disclosure is directed to devices, systems, and methods that address one or more of the disadvantages of the prior art.

SUMMARY

In an exemplary aspect, the present disclosure is directed to a surgical utility connector that is detectable by a surgical utility supplying device to indicate connection with the surgical utility supplying device. The surgical utility connector may include a first connecting region, a second connecting region, and a detection region between the first connecting region and the second connecting region. A utility channel may pass a utility from the surgical utility supplying device. The utility channel may extend through the first connecting region, the detection region, and the second connecting region. The surgical utility connector also may include a magnetic element disposed in the detection region and surrounding the utility channel. The magnetic element may have a magnetic field detectable by the surgical utility supplying device when the surgical utility connector is connected to the surgical utility supplying device.

In an aspect, the first connecting region may include a first connecting interface configured to engage a utility port of the surgical utility supplying device. The second connecting region may include a second connecting interface configured to engage a surgical implement. Further, the surgical utility supplying device is configured to supply the utility to the surgical implement via the utility channel of surgical utility connector. The surgical utility system is configured to determine whether the surgical utility connector is engaged to the utility port by detecting the magnetic element deposed in the detection region of the surgical utility connector.

In another exemplary aspect, the present disclosure is directed to a surgical utility system. The surgical utility system may include a surgical implement, a surgical utility supplying device configured to supply utility to the surgical implement, and a surgical utility connector configured to connect the surgical implement to the surgical utility supplying device.

The surgical utility connector may include a first connecting region configured to engage the surgical utility supplying device, a second connecting region configured to engage the surgical implement, a detection region disposed between the first connecting region and the second connecting region, a utility channel formed through the first connecting region, the detection region, and the second connecting region, and through which the utility is supplied from the surgical utility supplying device to the surgical implement, and a magnetic element disposed in the detection region and surrounding the utility channel.

The surgical utility supplying device may include a utility port configured to engage the first connecting region of the surgical utility connector, a hall-effect sensor configured to detect a presence of the magnetic element when the surgical utility connector is engaged to the utility port, and a processor configured to determine whether the surgical implement is engaged to the utility port based on the detection of the hall-effect sensor.

In still another exemplary aspect, the present disclosure is directed to a method including: receiving a surgical implement at a utility port of a surgical utility supplying device via a surgical utility connector, determining whether the surgical implement is connected to the surgical utility supplying device by detecting a magnetic element disposed in the surgical utility connector, and supplying utility to the surgical implement when the surgical implement is connected to the surgical utility supplying device.

In an aspect, the method may also include determining whether the surgical implement is connected to the surgical utility supplying device by detecting an RFID tag disposed in the surgical utility connector.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
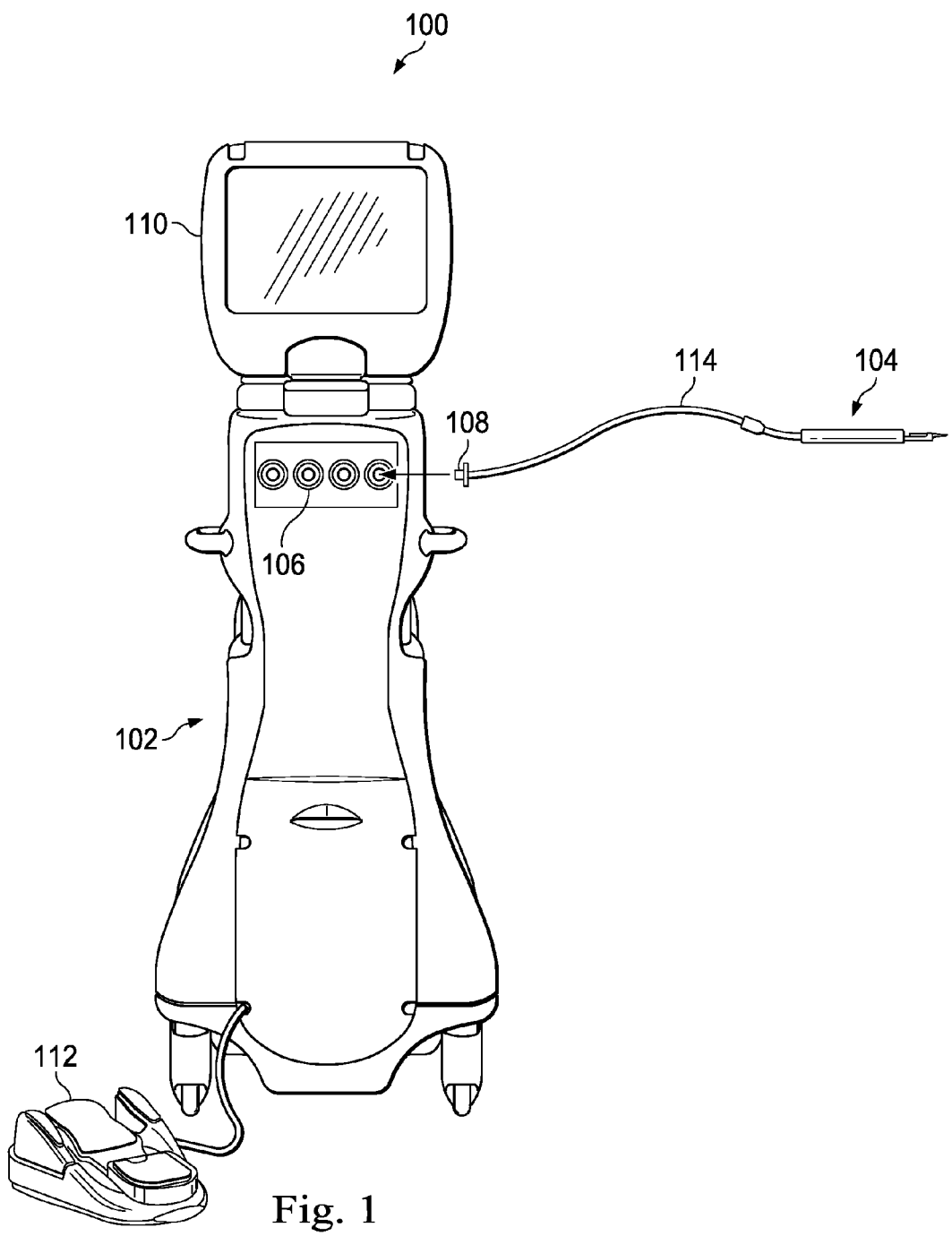
FIG. 1 illustrates a perspective view of an exemplary surgical system according to one embodiment consistent with the principles of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein provide a surgical utility connector embedded with a magnetic element that may be detected by a hall-effect sensor disposed in a surgical utility supplying device. When the surgical utility connector is connected to a utility port of the surgical utility supplying device, the surgical utility supplying device may detect the connection by detecting the magnetic element embedded in the surgical utility connector. In embodiments disclosed, this may allow the surgical utility supplying device to consistently detect the connection or disconnection of the surgical utility connector, even if a portion of the surgical utility connector is not configured to be inserted into the surgical utility supplying device. Moreover, unlike the RFID technique, continuous polling may not be needed, which may conserve device power and reduce processing load. Rather, the hall-effect sensor may output a voltage signal which may vary based on whether the magnetic element embedded in the surgical utility connector is present. The surgical utility supplying device may determine whether the surgical implement is properly connected based on the voltage signal output from the hall-effect sensor. Furthermore, surgical implements may be relatively easily disconnected from the surgical utility supplying device and replaced as desired, permitting relatively easy assembly, removal, and repair.

FIG. 1 illustrates an exemplary surgical system, generally designated 100. The surgical system 100 may include a surgical utility supplying device 102 with an associated display screen 110 showing data relating to system operation and performance during a surgical procedure. The surgical system 100 also may include a surgical implement 104 configured to be connected to the surgical utility supplying device 102 via a surgical utility connector 108. The surgical utility supplying device 102 may supply various utility, such as imaging light, compressed air, vacuum, pressurized liquid, or the like, to various kinds of surgical implements. For example, the surgical utility supplying device 102 may supply laser imaging light to an imaging probe or may supply pressurized liquid to a surgical irrigation tool. A user, e.g., a surgeon, may perform surgeries by using the surgical implements. The surgical utility supplying device 102 may include one or more utility ports 106 each configured to output a certain type of utility. Thus, multiple types of utilities may be supplied from the surgical utility supplying device 102 to multiple types of surgical implements 104 at the same time.

The utility may be output from a utility port 106 to the surgical utility connector 108 and be carried by a tube or cable (referenced herein as cable 114) to the surgical implement 104. The surgical implements 104 may selectively be attached or detached from the utility ports 106 by the surgical utility connectors 108. For example, a surgical implement 104 may be detached from the surgical utility supplying device 102 by detaching the surgical utility connector 108 from the utility port 106. The surgical utility supplying device 102 may detect a disconnection of a surgical implement 104 and may stop supplying utility to the surgical implement 104 to prevent mis-supply of utility. The surgical system 100 also may include a foot pedal 112 connected to the surgical system 100 for controlling the dispensing of utility from the surgical system 110. For example, a user may control the dispensing of the utility by selectively pressing and releasing the foot pedal 112.

Figure 2:
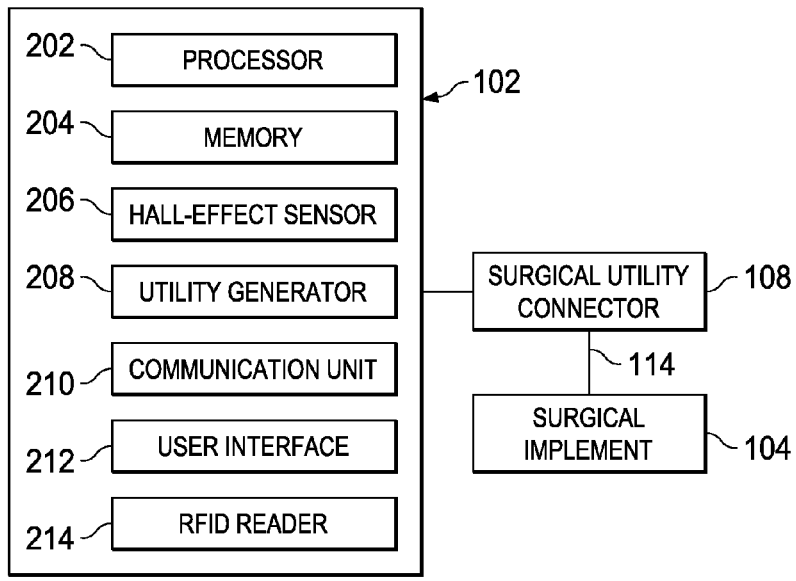
FIG. 2 illustrates a schematic diagram of an exemplary surgical utility supplying device according to an aspect consistent with the principles of the present disclosure.

FIG. 2 illustrates a schematic diagram of an exemplary surgical utility supplying device, e.g., the surgical utility supplying device 102. The surgical utility supplying device 102 may include a processor 202 configured to perform calculation and determination for controlling various operations of the surgical utility supplying device 102. The processor 202 may receive various signal inputs and make various determinations based on the signal inputs. For example, the processor 202 may receive signals from a hall-effect sensor configured to detect a presence of a magnetic element embedded in the surgical utility connector 108 to determine a connection status of the surgical implement 104. The processor 202 also may control the display screen 110 to display various information regarding the operations of the surgical utility supplying device 102 to notify various information to the user.

The surgical utility supplying device 102 may include a memory 204 configured to store information permanently or temporarily for various operations of the surgical utility supplying device 102. For example, the memory 204 may store programs that may be executed by the processor 202 to perform various functions of the surgical utility supplying device 102. The memory 204 also may store various data relating to operation history, user profile or preferences, various operation and surgical settings, and the like. Programs and information stored in the memory 204 may continuously be updated to provide customization and improvement in the operation of the surgical utility supplying device 102. The memory 204 also may include programs and information relating to operational parameters implemented based on the connection status of the surgical utility connector 108 and the utility ports 106.

The surgical utility supplying device 102 also may include a hall-effect sensor 206. The hall-effect sensor 206 may be configured to detect a presence of a magnetic element. For example, the hall-effect sensor 206 may be positioned near a utility port 106 to detect a magnetic element embedded in a surgical utility connector 108 when the surgical utility connector 108 is attached to the utility port 106. The hall-effect sensor 206 may output a voltage signal based on whether the magnetic element is detected. For example, the hall-effect sensor 206 may output a low or zero voltage signal when no magnetic element is detected and may output a high voltage signal when the magnetic element is detected. The signals output from the hall-effect sensor 206 may be received by the processor 202 to make determination of the connection status of the surgical implement 104.

The surgical utility supplying device 102 may include a utility generator 208. The utility generator 208 may include motors, light emitting devices, pumps, and the like that may generate various utilities, such as pressured liquid, compressed air, imaging light, and the like. In an embodiment, the utility generator 208 may be connected to an external utility source to receive utility externally. For example, the utility generator 208 may be connected to a vacuum source or an air compressor to receive vacuum or compressed air. The utility generator 208 may supply various utilities to respective utility ports 106.

The surgical utility supplying device 102 may include a communication unit 210. The communication unit 210 may include various communication devices, such as Ethernet card, wi-fi communication device, telephone device, digital I/O (Input/Output) ports or the like, that may allow the surgical utility supplying device to send and receive information to and from other devices. For example, the communication unit 210 may receive input from other surgical devices to coordinate a surgical operation. In another example, the communication unit 210 may transmit and receive messages or notifications, such as email, text, or other messages or notifications to a user's mobile device to notify certain information to the user.

The surgical utility supplying device 102 also may include a user interface 212. The user interface 212 may include user input devices, such as a keyboard, a touch screen, the foot pedal 112, a mouse, a microphone, or the like that allow a user to input instructions to the surgical utility supplying device 212. For example, the user may enter parameters for a utility and operate the foot pedal 112 to dispense the utility to the surgical implement 104. The user interface 212 also may include user output devices, such as a display screen 110, an audio speaker, LED (Light Emitting Diode) lights, or other visual or tactile signals that convey information to a user. For example, an audio speaker may emit an alarm when a surgical implement 104 is accidentally detached from the surgical utility supplying device 102 during a surgical operation. Thus, the user interface 212 enables a user to interact with the surgical utility supplying device 102 during surgical operations.

The surgical utility supplying device 102 further may include an RFID reader 214. The RFID reader 214 may be positioned at the utility port 106 and configured to detect and read RFID tags embedded in or otherwise associated with the surgical utility connector 108. The RFID tag or RFID reader 214 may have or may access a memory that stores information that identifies the type of surgical utility connector or surgical implement connected to the surgical utility connector. For example, when the surgical utility connector 108 is connected to the utility port 106 of the surgical utility supplying device 102, the surgical utility supplying device 102 may use the RFID reader 214 to read the RFID tag embedded in the surgical utility connector 108 to determine the type of surgical utility connector or the type of surgical implement connected to the surgical utility connector. Thus, the surgical utility supplying device 102 may determine the type of surgical utility connector or the type of surgical implement that is connected to the utility port 106.

Figure 3:
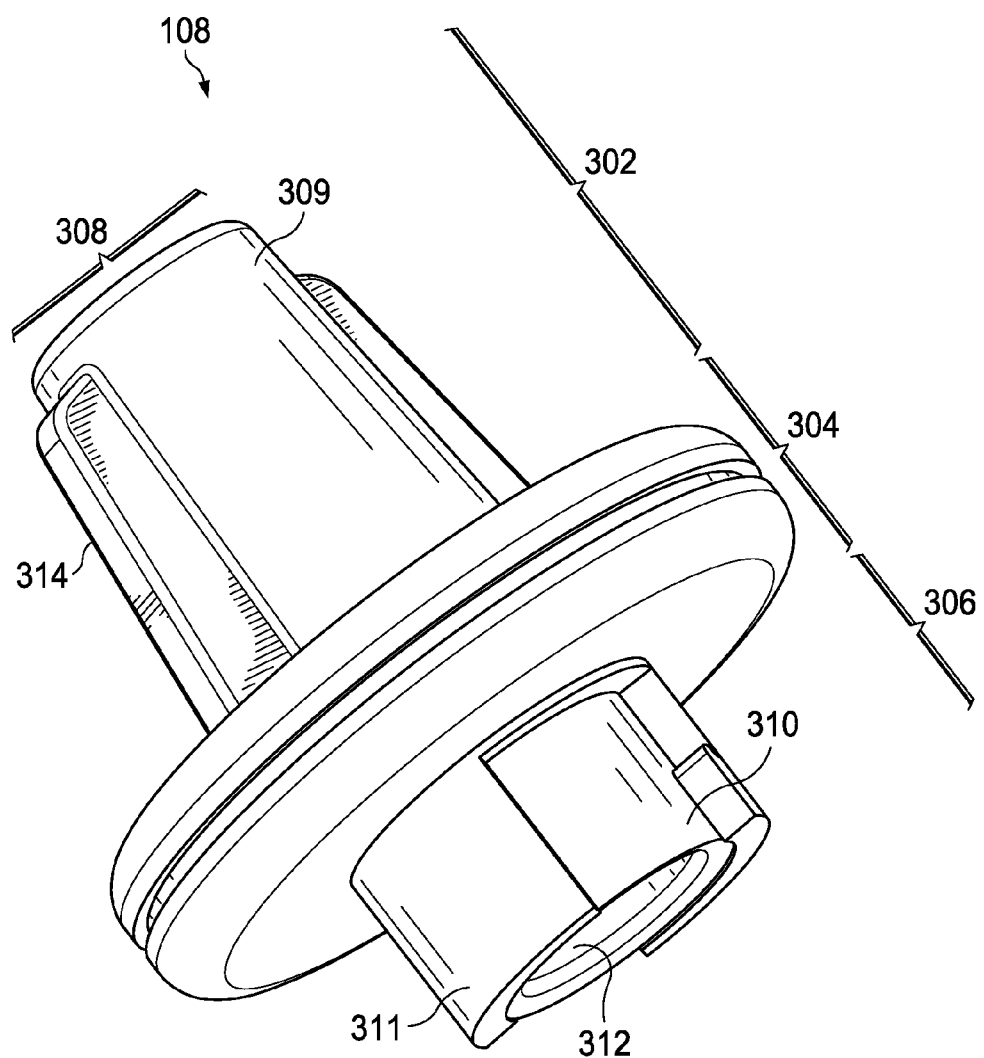
FIG. 3 illustrates a perspective view of an exemplary surgical utility connector according to an aspect consistent with the principles of the present disclosure.
Figure 4:
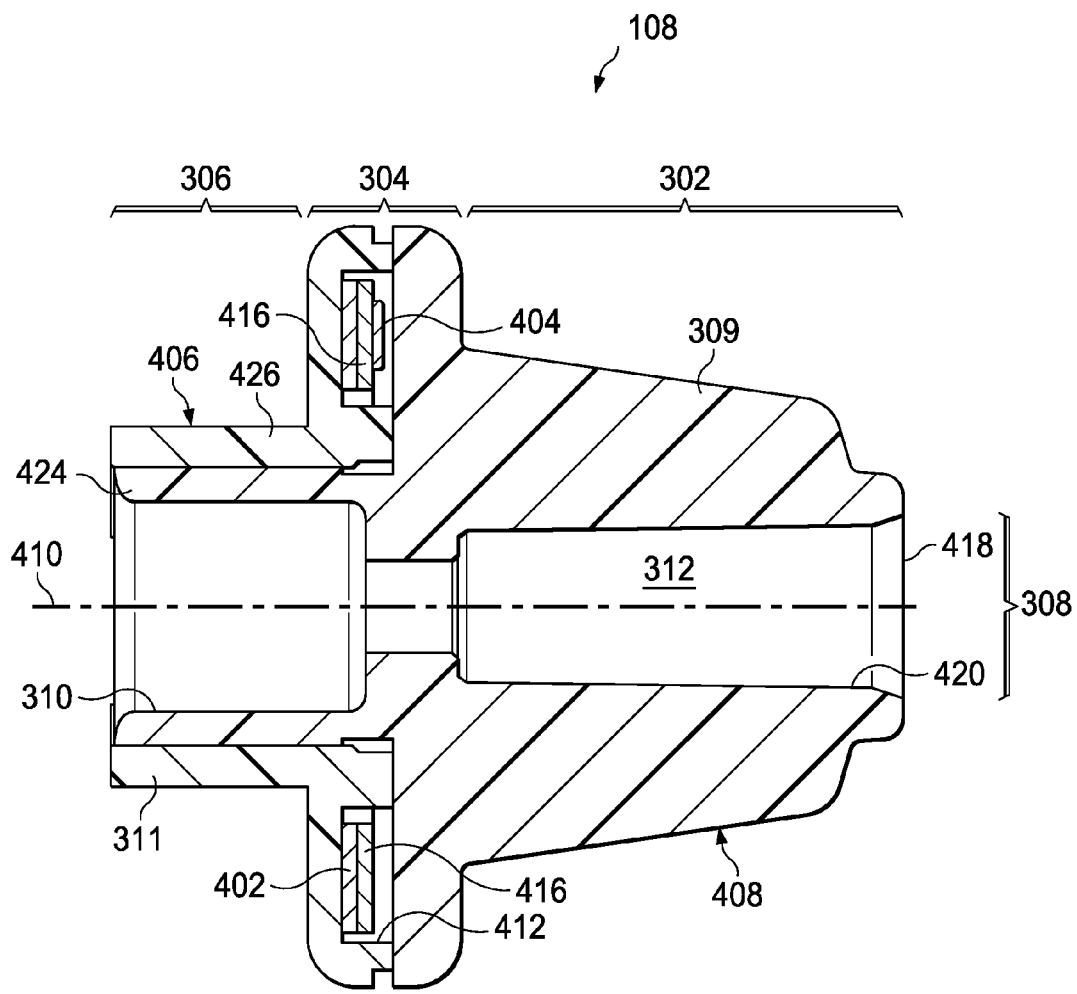
FIG. 4 illustrates a cross-sectional view of an exemplary surgical utility connector according to an aspect consistent with the principles of the present disclosure.

FIGS. 3 and 4 illustrate an exemplary surgical utility connector in greater detail. FIG. 3 illustrates a perspective view and FIG. 4 illustrates a cross-sectional view of the surgical utility connector 108. The surgical utility connector 108 may include a first connecting region 306, a second connecting region 302, and a detection region 304 disposed between the first connecting region 306 and the second connecting region 302.

The surgical utility connector 108 may be formed in part of non-metal material, such as plastic material. As shown in FIG. 4, a first shell 406 may be a plastic shell that forms the outer shell of the first connecting region 306 and a portion of the detection region 304. A second shell 408 may be another plastic shell that forms the second connecting region 302, a portion of the detection region 304, and an inner portion of the first connecting region 306. The first shell 406 and the second shell 408 may be coupled to each other to form the surgical utility connection 108.

The first connecting region 306 may include a first connection interface 310 configured to engage and connect to a utility port 106 of the surgical utility supplying device 102. The first connecting interface 310 may include a cylindrical body 311 and grooves and protrusions formed on an external surface of the cylindrical body 311. The grooves and protrusions may be configured to match a configuration of a utility port 106 to securely attach or lock the surgical utility connector 108 to the utility port 106 of the surgical utility supplying device 102.

The second connecting region 302 may include a second connecting interface 308 configured to engage and connect to a surgical implement 104 (FIG. 1) or a cable 114 attached to the surgical implement 104. As shown in FIG. 4, the second connecting interface 308 may include an opening 418 and a gradual tapered receiver 420 configured to receive a proximal end of the cable 114 into a portion of a utility channel 312 at the first connecting region 302. Thus, the proximal end of the cable 114 may be inserted into the utility channel 312 at the second connecting region 302. The opening 418 and the tapered receiver 420 may be configured to achieve water and/or air seal between the surgical utility connector 108 and the cable 114 when they are connected, such that the utility, e.g., air or liquid, do not leak out at the connection interface.

The second connecting region 302 also may include one or more protrusions 314 positioned on the outer surface of the second connecting region 302. The protrusions 314 may protrude from the outer surface. Thus, when a user is inserting the surgical utility connector 108 into the utility port 106, the protrusion 314 may function as torque wings that facilitate a twisting motion of the surgical utility connector 108 by the user's finger and thumb to lock the surgical utility connector 108 to the utility port 106.

The utility channel 312 may extend through the first connecting region 306, the detection region 304, and the second connecting region 302. The utility channel 312 may be configured to allow a utility to pass from the surgical utility supplying device 102 attached to the first connecting region 306 and to the cable 114 attached to the second connecting region 302 for conveyance to the surgical implement 104.

As shown in FIG. 4, the utility channel 312 may be formed through the first connection interface 310 of the first connecting region 306 in a direction of a longitudinal axis 410 of the cylindrical body of the first connecting region 306. The utility channel 312 also may be formed through a cylindrical body 309 of the second connecting region 302 in a direction of longitudinal axis 410 of the cylindrical body 309 of the second connecting region 302. The detection region 304 may have a disk-shape and the utility channel 312 may be formed through the disk-shape in a direction of a center axis of the disk shape. The longitudinal axis 410 of the first and the second connecting regions 306 and 302 and the center axis (not shown) of the detection region 304 may be coaxially aligned to each other. Here, the utility channel 312 may include three segments respectively positioned at the first connecting region 306, the detection region 304, and the second connecting region 302. A radius of the utility channel 312 at the first connecting region 306 may be greater than a radius of the utility channel 312 at the second connecting region 302. Further, the radius of the utility channel 312 at the second connecting region 302 may be greater than a radius of the utility channel 312 at the detection region 304.

As shown in FIG. 4, the second connecting region 302, a portion of the detection region 304, and an inner portion 424 of the first connecting region 306 may be formed integrally as the second shell 408. An external shell 426 of the first connection portion 306 and a portion of the detection region 304 may be formed integrally as the first shell 406. The first and second shells 406 and 408 may be coupled to each other by inserting the inner portion 424 of the first connecting region 306 into the external shell 426 of the first connection portion 306.

The surgical utility connector 108 may include a magnetic element 402 configured to emit a magnetic field detectable by the hall-effect sensor 206 of the surgical utility supplying device 102 when the surgical utility connector 108 is attached to a utility port 106. An inner groove 412 may be formed at the detection region 304 to receive the magnetic element 402. An RFID tag 404 and an RFID Printed Circuit Board (PCB) 416 also may be provided in the inner groove 412 along with the magnetic element 402. The RFID tag 404 may identify, for example, the type of the surgical utility connector 108 and the corresponding surgical implement 104. The RFID printed circuit board 416 may include an RFID antenna and circuits configured to receive and respond to signals from RFID readers.

Figure 5:
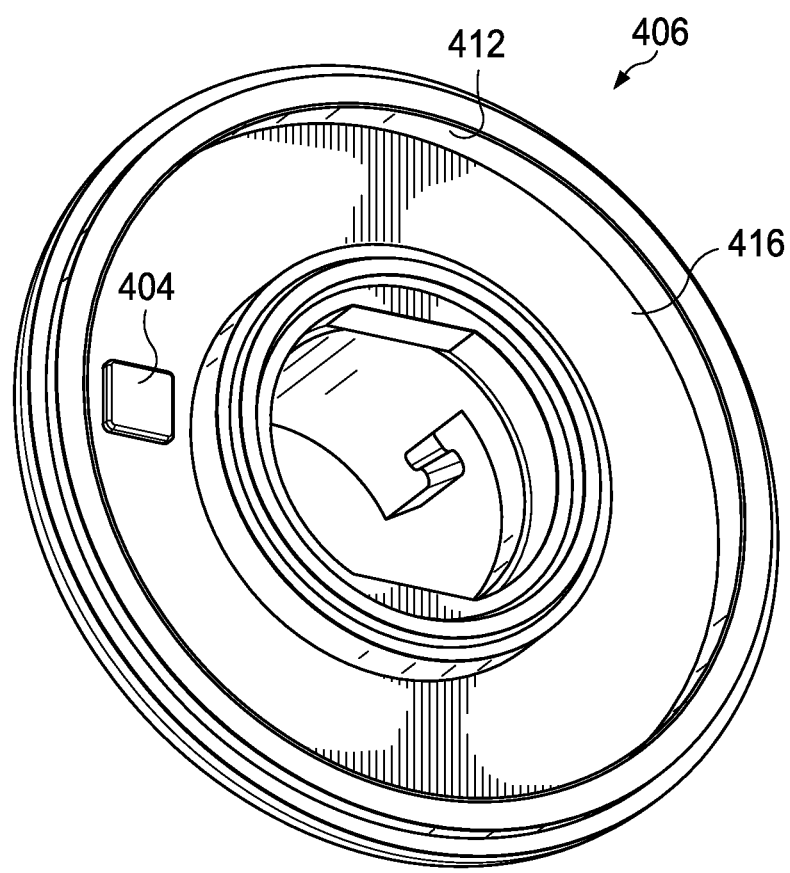
FIG. 5 illustrates a perspective view of internal components of an exemplary surgical utility connector according to an aspect consistent with the principles of the present disclosure.

FIG. 5 illustrates a perspective view of the first shell 406 and internal components of an exemplary surgical utility connector 108. The first shell 406 may include the inner groove 412 to accommodate the magnetic element 402. The magnetic element 402 may have a ring shape such that the utility channel 312 may pass through a center of the ring-shaped magnetic element 402.

The RFID tag 404 and the RFID PCB 416 also may be accommodated in the inner groove 412. The RFID PCB 416 may have a ring shape similar to the ring shape of the magnetic element 402. The RFID PCB 416 and the magnetic element 402 may be disposed adjacent to each other in the groove, such that they form one ring shape with two layers, e.g., one layer of the magnetic element 402 and one layer of the RFID PCB 416. The RFID tag 404 may be connected to the RFID PCB 416. The RFID PCB 416 may be disposed closer to the first connecting region 306 than the magnetic element 402 is disposed to the first connecting region 306. In some embodiments, the magnetic element 402 may be disposed closer to the first connecting region 306 than the RFID PCB 416 is disposed to the first connecting region 306.

The RFID scanner/reader 214 (FIG. 2) may be configured to detect and read the RFID tag 404 when the surgical utility connector 108 is connected to the utility port 106. Thus, the surgical utility supplying device 102 may read the RFID tag 404 of the surgical utility connector 108 to determine the type of surgical implement 104 connected to the corresponding surgical utility connector 108. For example, the RFID tag 404 may have a memory that stores the identification and description of the surgical utility connector 108 and its corresponding surgical implement 104. This information may be communicated to the surgical utility supplying device 102 for operation. Alternatively, the RFID tag 404 may provide an identifying indicator, and the surgical utility supplying device 102 may look up the identification and description based on the indicator.

Figure 8:
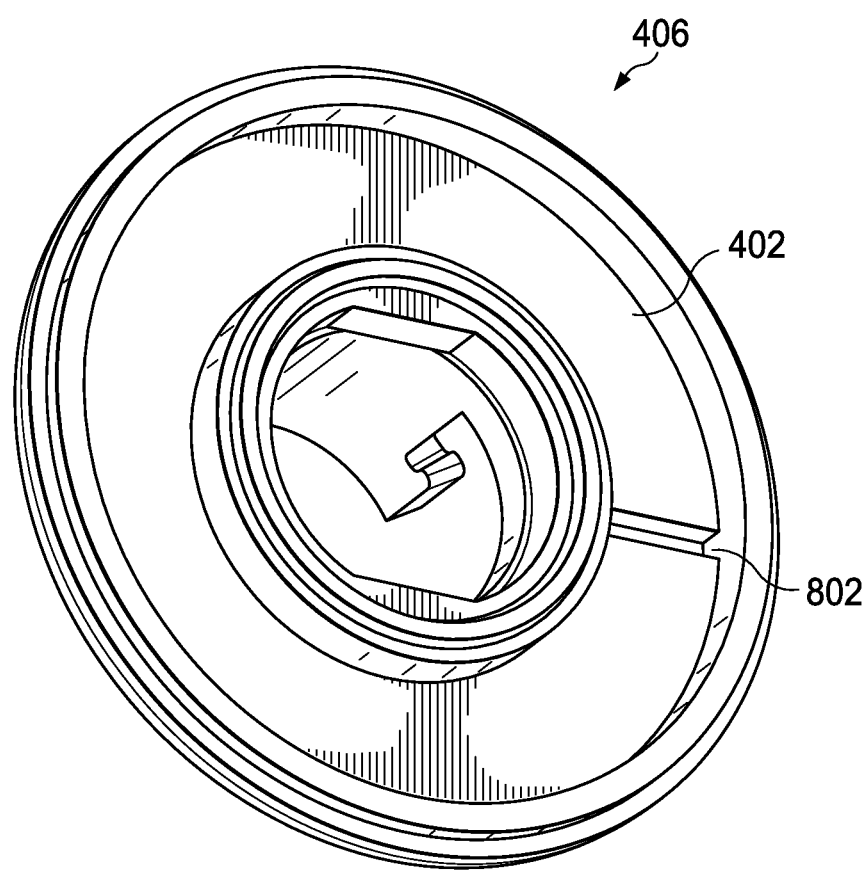
FIG. 8 illustrates a perspective view of internal components of an exemplary surgical utility connector according to an aspect consistent with the principles of the present disclosure.

As shown in FIG. 8, some embodiments of the ring-shaped magnetic element 402 may include a gap or a cutout 802, such that the magnetic element 402 does not form a continuous ring shape. In some instance, the magnetic field of the magnetic element 402 may interfere with the RFID communication between the RFID tag 404 and the RFID scanner/reader. The gap 802 in the magnetic element 402 may reduce the interference of the magnetic field to the RFID reader 214.

Figure 6:
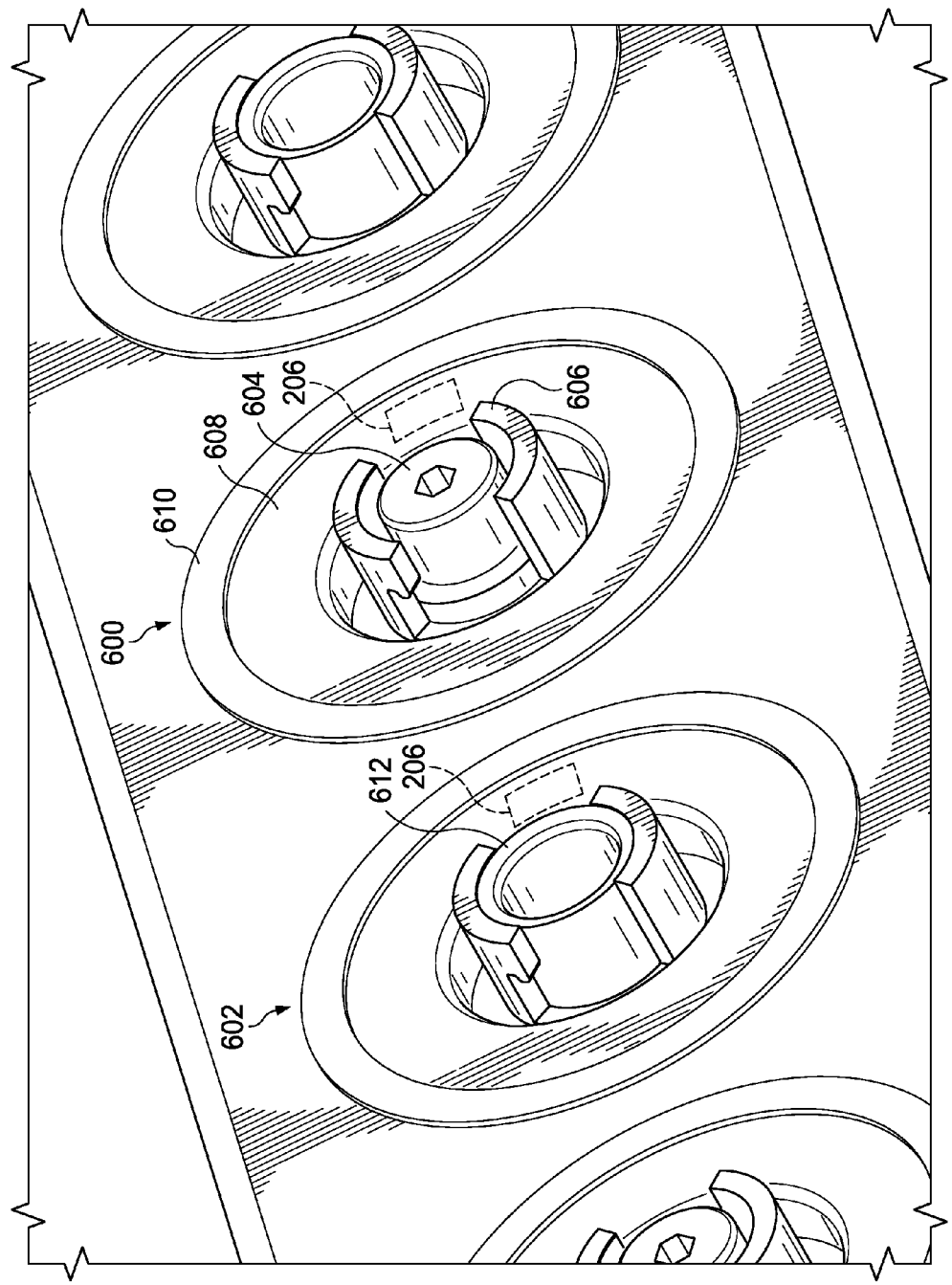
FIG. 6 illustrates a perspective view of exemplary utility ports according to an aspect consistent with the principles of the present disclosure.

FIG. 6 illustrates a perspective view of exemplary utility ports 106. The surgical utility supplying device 102 may include multiple utility ports 106. Each utility port 106 may be configured to supply a specific utility. For example, there may be one utility port 106 that supplies compressed air, another that supplies pressurized liquid, and another that supplies vacuum for conveyance to an appropriate probe or handpiece. Each type of utility port 106 may have its own unique connection interface. There may be male or female types of connection interface. For example, a connection interface for a vacuum utility port may be different from a connection interface for a pressurized liquid utility port. Thus, different types of surgical utility connectors 108 may match different types of utility ports 106. For example, a surgical utility connector 108 for a surgical implement 104 that utilizes vacuum may be configured to match a connection interface of a vacuum utility port and may not match a connection interface of a pressurized liquid utility port. Thus, a user may be prevented from connecting a surgical implement 104 into the wrong utility port.

In some exemplary aspects, a utility port 600 may have a male type connection interface configured to receive a female type surgical utility connector 108. The utility port 600 may include a circular rib 610 surrounding and defining a port surface 608. The circular rib 610 may include lighting elements that emit different colors of light to indicate the status of the utility port 600. In particular, the circular rib 610 may have LED lighting elements covered by relatively opaque, e.g., clear, white, or gray, ring-shape cover. The processor 202 may control the LED lighting elements to selectively emit different colors of light based on a status of the utility port 600. For example, the lighting elements of the circular rib 610 may emit an amber color light to indicate that a wrong surgical utility connector is attached to the utility port 600, a green light to indicate that a correct surgical utility connector is properly attached to the utility port 600, a blue light to indicate that the utility port 600 is ready for connection, and light off to indicate that the utility port 600 is not in service.

The utility port 600 also may include a protruding body 604 and interlocking walls 606. The surgical utility connector 108 may be placed on the port surface 608 with the first connecting region 306 coupled to the protruding body 604 and the interlocking walls 606 of the utility port 600. In particular, the first connecting region 306 may be inserted in a space between the protruding body 604 and the interlocking walls 606. The protruding body 604 may be received into the utility channel 312 of the first connecting region 306.

In the example shown, the grooves of the first connection interface 310 of the first connecting region 306 may have a shape matching the interlocking walls 606 of the utility port 600 to receive the interlocking walls 606. In some embodiments, the grooves of the first connection interface 310 have an L-shape, although other interlocking shapes are contemplated. When the surgical utility connector 108 is engaging the utility port 600, the interlocking walls 606 of the utility port 600 may slide in the L-shaped groove and the interlocking walls 606 may interlock into the grooves of the first connection interface 310 with a rotation or twist of the surgical utility connector 108 about the longitudinal axis 410. When the surgical utility connector 108 is properly connected to the utility port 600, the detection region 304 of the surgical utility connector 108 may be positioned on the port surface 608 and surrounded by the circular rib 610. The circular rib 610 may be configured to restrict movement of the surgical utility connector 108 on the port surface 608 to prevent accidental disconnection. The hall-effect sensor 206 may be disposed below the port surface 608 to detect the magnetic element 402 embedded in the detection region 304 of the surgical utility connector 108. The RFID reader 214 also may be disposed below the port surface 608 to detect and read the RFID tag 404 embedded in the detection region 304 of the surgical utility connector 108.

A utility port 602 may be similar to utility port 600 but with a female type connection interface 612. As shown in FIG. 6, utility port 602 may have a connection interface similar to the first connection interface 310 of the surgical utility connector 108 shown in FIG. 3. Thus, utility port 602 may be configured to connect with a male-type surgical utility connector. A male-type surgical utility connector may be similar to the surgical utility connector 108, but with a first connection interface including a protruding body and interlocking walls similar to the protruding body 604 and the interlocking walls 606 of the male-type utility port 600. Thus, the female-type utility port 602 may be configured to receive a male-type surgical utility connector.

The hall-effect sensor 206 may be disposed at each of the utility ports 600 and 602 to detect connection of respective surgical utility connector 108 to each utility port 106. The magnetic element 402 embedded in the surgical utility connector 108 may have a magnetic field of a specific strength, such that the hall-effect sensor 206 may detect the magnetic element 402 when the surgical utility connector 108 is properly connected to the utility port 106 and may not detect the magnetic element 402 when the surgical utility connector 108 is disconnected or begins to separate from the utility port 106. Thus, the hall-effect sensor 206 may detect the magnetic element 402 when the surgical utility connector 108 is properly connected to the utility port 106. Further, the hall-effect sensor 206 may detect the disconnection of the surgical utility connector 108 when the surgical utility connector 108 is detached from the utility port 106 or when the surgical utility connector 108 is not properly connected to the utility port 106.

Figure 7:
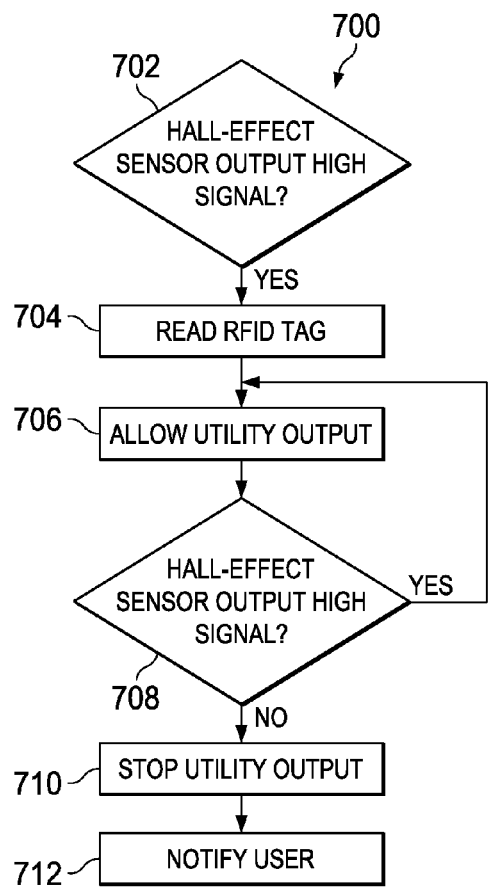
FIG. 7 is a flow chart illustrating a method for detecting a magnetic element embedded in a surgical utility connector according to an aspect consistent with the principles of the present disclosure.

FIG. 7 is a flow chart illustrating a method 700 for detecting a connection of a surgical utility connector. At 702, the hall-effect sensor 206 may detect a connection status of the surgical utility connector 108 by detecting the presence of the magnetic element 402. For example, when a user plugs the surgical utility connector 108 into a utility port 106, the hall-effect sensor 206 may detect the magnetic field emitted from the magnetic element 402 and begin to output a high voltage signal. A high voltage signal may be a voltage that is greater than a predetermined threshold voltage. The threshold voltage may be predetermined such that when the surgical utility connector 108 is properly connected to the utility port 106 the output voltage of the hall-effect sensor 206 is greater than the threshold voltage. Thus, the surgical utility supplying device 102 may read the voltage output from the hall-effect sensor 206 to determine whether the surgical utility supplying device 102 is properly connected to the utility port 106.

If the surgical utility supplying device 102 determines that the hall-effect sensor 206 outputs a low voltage signal, the surgical utility supplying device 102 may prohibit the output of the utility through the utility port 106. For example, if no surgical utility connector is connected to the utility port 106, utility may not be supplied to the utility port 106.

If the surgical utility supplying device 102 determines that the hall-effect sensor 206 outputs a high voltage signal, the surgical utility supplying device 102 may read an RFID tag 404 embedded in the surgical utility connector 108 at 704 to confirm that the correct type of surgical utility connector is connected to the utility port 106. The RFID tag 404 or the surgical utility supplying device 102 may have a memory that stores identity information and a description of the type of surgical utility connector that may represent the type of associated handpiece or surgical implement. In some aspects, the RFID tag may store instrument identification or parameters of the surgical implement. For example, the RFID tag 404 or the surgical utility supplying device 102 may store surgical parameters, such as preferred range of flow rate, pressure, intensity of utility for a specific surgical implement. For example, the RFID tag 404 or the surgical utility supplying device 102 may indicate that the surgical utility connector is for supplying a pressurized liquid to a surgical implement. Thus, the RFID reader 214 that may read the RFID tag 404 may confirm that the utility port 106 to which the surgical utility connector 108 is connected is configured to supply the pressurized liquid. Accordingly, supply of utility to the wrong surgical implement may be prevented.

At 706, the surgical utility supplying device 102 may allow the supply of utility through the utility port 106. In particular, when the user activates a control, e.g., the foot pedal 112, the surgical utility supplying device 102 may output the utility through the utility port 106 to the surgical implement 104, because the surgical utility connector 108 is properly connected to the utility port 106.

At 708, the surgical utility supplying device 102 may determine whether the surgical utility connector 108 is properly connected to the utility port 106 by detecting whether the hall-effect sensor 206 still outputs the high voltage signal. If the hall-effect sensor 206 continues to detect the magnetic element 402 of the surgical utility connector 108, the hall-effect sensor 206 may continue to output the high voltage signal and the surgical utility supplying device 102 may determine that the surgical utility connector 108 still is properly connected to the utility port 106. Thus, the surgical utility supplying device 102 may continue to allow utility output at 706.

If the surgical utility supplying device 102 determines that the hall-effect sensor outputs a low voltage signal, the surgical utility supplying device 102 may immediately stop supply of utility through the utility port 106 at 710. For example, during a surgical operation, if a surgical implement 104 is accidentally disconnected, the surgical utility supplying device 102 may immediately stop the supply of utility to prevent spill over.

At 712, the surgical utility supplying device 102 may notify the user that the surgical utility connector 108 is disconnected or is not properly connected to the surgical utility supplying device 102. For example, a message may be displayed on the display screen 110 to notify the user or a sound alert may be generated by a speaker or other alert may be used to alert the user.

By using a hall-effect sensor to detect the presence of a magnetic element embedded in a surgical utility connector, various types of surgical utility connectors may be detected, including surgical utility connectors that do not have a portion configured to be inserted through a utility port. Further, by using a hall-effect sensor, continuous polling is not required to monitor a connection status of the surgical utility connector.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A surgical utility connector detectable by a surgical supplying device to indicate connection with the surgical supplying device, comprising:
   a first connecting region;
   a second connecting region;
   a detection region between the first connecting region and the second connecting region;
   a utility channel configured to carry utility within the utility channel from the surgical supplying device, the utility channel extending through the first connecting region, the detection region, and the second connecting region; and
   a magnetic element disposed in the detection region and surrounding the utility channel, the magnetic element having a field detectable by the surgical supplying device when the surgical utility connector is connected to the surgical supplying device;
   wherein the first connecting region comprises a first cylindrical body and the utility channel is formed through the first cylindrical body in a direction of a cylindrical axis of the first cylindrical body;
   wherein the second connecting region comprises a second cylindrical body and the utility channel is formed through the second cylindrical body in a direction of a cylindrical axis of the second cylindrical body; and
   wherein the detection region comprises a disk body and the utility channel is formed through the disk body in a direction of a center axis of the disk body;
   wherein the disk body has a greater radius than that of the first cylindrical body and the second cylindrical body.

2. A surgical utility connector detectable by a surgical supplying device to indicate connection with the surgical supplying device, comprising:
   a first connecting region;
   a second connecting region;
   a detection region between the first connecting region and the second connecting region;
   a utility channel configured to carry utility within the utility channel from the surgical supplying device, the utility channel extending through the first connecting region, the detection region, and the second connecting region; and
   a magnetic element disposed in the detection region and surrounding the utility channel, the magnetic element having a field detectable by the surgical supplying device when the surgical utility connector is connected to the surgical supplying device;
   wherein the first connecting region comprises a first cylindrical body and the utility channel is formed through the first cylindrical body in a direction of a cylindrical axis of the first cylindrical body;
   wherein the second connecting region comprises a second cylindrical body and the utility channel is formed through the second cylindrical body in a direction of a cylindrical axis of the second cylindrical body; and
   wherein the detection region comprises a disk body and the utility channel is formed through the disk body in a direction of a center axis of the disk body;
   wherein a radius of the utility channel through the detection region is less than a radius of the utility channel through the first connecting region.

3. A surgical utility connector detectable by a surgical supplying device to indicate connection with the surgical supplying device, comprising:
   a first connecting region;
   a second connecting region;
   a detection region between the first connecting region and the second connecting region;
   a utility channel configured to carry utility within the utility channel from the surgical supplying device, the utility channel extending through the first connecting region, the detection region, and the second connecting region; and
   a magnetic element disposed in the detection region and surrounding the utility channel, the magnetic element having a field detectable by the surgical supplying device when the surgical utility connector is connected to the surgical supplying device;
   wherein the magnetic element comprises a ring-shaped body disposed in the detection region and the utility channel passes through a center of the ring-shaped body of the magnetic element;
   further comprising a Radio-Frequency Identification (RFID) tag disposed in the detection region, wherein the RFID tag identifies the surgical utility connector.

4. The surgical utility connector of claim 3, wherein the ring-shaped body of the magnetic element has a gap such that the magnetic element does not form a complete ring shape.

5. A surgical system comprising:
   a surgical implement;

a surgical utility supplying device configured to supply a utility to the surgical implement;
a surgical utility connector configured to connect the surgical implement to the surgical utility supplying device;
wherein the surgical utility connector comprises:
a first connecting region configured to engage the surgical utility supplying device;
a second connecting region configured to engage the surgical implement;
a detection region disposed between the first connecting region and the second connecting region;
a utility channel formed through the first connecting region, the detection region, and the second connecting region, and through which the utility is supplied from the surgical utility supplying device to the surgical implement; and
a magnetic element disposed in the detection region and surrounding the utility channel,
wherein the surgical utility supplying device comprises:
a utility port configured to engage the first connecting region of the surgical utility connector;
a hall-effect sensor configured to detect a presence of the magnetic element when the surgical utility connector is engaged to the utility port;
a processor configured to determine whether the surgical implement is engaged to the utility port based on the detection of the hall-effect sensor.

6. The surgical system of claim 5, wherein the magnetic element of the surgical utility connector comprises a ring-shaped body disposed in the detection region and the utility channel passes through a center of the ring-shaped body.

7. The surgical system of claim 5, wherein the hall-effect sensor is disposed at the utility port to detect the magnetic element of the surgical utility connector when the surgical utility connector is engaged to the utility port.

8. The surgical system of claim 5,
wherein the surgical utility connector further comprises a Radio-Frequency Identification (RFID) tag disposed in the detection region, and
wherein the surgical utility supplying device further comprises an RFID detecting device configured to detect and read the RFID tag.

9. The surgical system of claim 6, wherein the ring-shaped body of the magnetic element has a gap such that the magnetic element does not form a complete ring shape.

10. The surgical system of claim 5, wherein the utility is compressed air.

11. The surgical system of claim 5, wherein the utility is pressurized liquid.

12. The surgical system of claim 5, wherein the surgical utility supplying device is configured to stop supplying the utility when the processor determines that the surgical utility connector is disengaged from the utility port.

* * * * *